US012806073B2

(12) United States Patent
Gliner et al.

(10) Patent No.: US 12,806,073 B2
(45) Date of Patent: Nov. 24, 2026

(54) PHACOEMULSIFICATION SYSTEM WITH AUTOMATIC DETECTION OF EXTENSION TUBING

(71) Applicant: JOHNSON & JOHNSON SURGICAL VISION, INC., Irvine, CA (US)

(72) Inventors: Vadim Gliner, Haifa (IL); Assaf Govari, Haifa (IL)

(73) Assignee: Johnson & Johnson Surgical Vision, Inc., Irvine, CA (US)

( * ) Notice: Subject to any disclaimer, the term of this patent is extended or adjusted under 35 U.S.C. 154(b) by 853 days.

(21) Appl. No.: 18/106,608

(22) Filed: Feb. 7, 2023

(65) Prior Publication Data

US 2023/0285190 A1 Sep. 14, 2023

Related U.S. Application Data

(60) Provisional application No. 63/317,674, filed on Mar. 8, 2022.

(51) Int. Cl.
*A61F 9/007* (2006.01)
*A61B 17/00* (2006.01)

(52) U.S. Cl.
CPC *A61F 9/00745* (2013.01); *A61B 2017/00973* (2013.01)

(58) Field of Classification Search
CPC ...... A61M 1/72; A61M 1/71; A61M 2205/12; A61M 2205/121; A61M 2207/00; A61B 2217/005; A61B 2217/007; A61F 9/00745
See application file for complete search history.

(56) References Cited

U.S. PATENT DOCUMENTS 4,256,442 A * 3/1981 Lamadrid ........... F04B 43/1284 417/475
5,755,691 A * 5/1998 Hilborne ............... A61M 5/142 417/474
5,993,420 A * 11/1999 Hyman ................. A61M 5/365 604/503

(Continued)

FOREIGN PATENT DOCUMENTS

WO 2020157723 A2 8/2020

OTHER PUBLICATIONS

Hurricane Medical Ophthalmology Surgical Instruments International Distributor. Cortex Removal Accessed via Wayback Machine Oct. 16, 2025 (Year: 2019).*

*Primary Examiner* — Scott J Medway

(57) ABSTRACT

A phacoemulsification system includes a phacoemulsification handpiece, an irrigation line and an aspiration line connected to the phacoemulsification handpiece, an Anti-Vacuum Surge (AVS) module inserted at least in the aspiration line, and a processor. The processor is configured to automatically detect whether an extension tubing is present in the aspiration line between the phacoemulsification handpiece and the AVS module, to set a first parameter setting, for detecting vacuum surges in the aspiration line, in response to detecting that the extension tubing is present, and, in response to detecting that the extension tubing is not present, to set a second parameter setting, different from the first parameter setting, for detecting the vacuum surges in the aspiration line.

16 Claims, 3 Drawing Sheets

(56) References Cited

U.S. PATENT DOCUMENTS

| | | | | |
|---|---|---|---|---|
| 6,560,062 | B1 * | 5/2003 | Kovacs | G11B 15/32 360/96.51 |
| 6,629,955 | B2 * | 10/2003 | Morris | A61M 5/14228 604/153 |
| 7,070,578 | B2 * | 7/2006 | Leukanech | A61M 1/72 292/201 |
| 7,297,137 | B2 | 11/2007 | Gordon et al. | |
| 7,303,566 | B2 | 12/2007 | Kishimoto et al. | |
| 7,914,482 | B2 | 3/2011 | Urich et al. | |
| 9,603,990 | B2 * | 3/2017 | Woolford | F04B 43/0072 |
| 9,713,660 | B2 * | 7/2017 | Baxter | A61M 1/72 |
| 11,351,365 | B1 * | 6/2022 | McKeag | A61N 1/36071 |
| 2004/0202561 | A1 * | 10/2004 | Hershberger | F04B 43/1253 417/477.7 |
| 2005/0118048 | A1 * | 6/2005 | Traxinger | A61M 1/72 417/477.2 |
| 2007/0261214 | A1 * | 11/2007 | Nerbonne | A61M 39/284 24/326 |
| 2010/0292631 | A1 | 11/2010 | Holden | |
| 2012/0157943 | A1 | 6/2012 | Sorensen et al. | |
| 2012/0164006 | A1 * | 6/2012 | Moy | F04B 43/08 417/360 |
| 2012/0271233 | A1 * | 10/2012 | Bruggemann | A61M 5/14546 604/131 |
| 2013/0071272 | A1 * | 3/2013 | Juretich | F04B 43/1261 417/477.2 |
| 2013/0267894 | A1 * | 10/2013 | Woolford | A61B 18/148 604/67 |
| 2014/0163455 | A1 * | 6/2014 | Wilson | A61M 1/774 604/28 |
| 2015/0359666 | A1 * | 12/2015 | Zacharias | A61M 1/75 604/151 |
| 2016/0074565 | A1 * | 3/2016 | Giordano | A61M 1/36224 210/85 |
| 2016/0166742 | A1 | 6/2016 | Layser et al. | |
| 2018/0177945 | A1 * | 6/2018 | Sims | G16H 20/17 |
| 2019/0099546 | A1 | 4/2019 | Keh et al. | |
| 2021/0128808 | A1 * | 5/2021 | Dandler | A61M 1/16 |
| 2022/0192876 | A1 | 6/2022 | Algawi et al. | |
| 2022/0362056 | A1 * | 11/2022 | Algawi | A61M 1/77 |
| 2022/0362452 | A1 * | 11/2022 | Algawi | F04B 15/00 |
| 2024/0293609 | A1 * | 9/2024 | Loomis | F04B 43/08 |

* cited by examiner

PHACOEMULSIFICATION SYSTEM WITH AUTOMATIC DETECTION OF EXTENSION TUBING

CROSS-REFERENCE TO RELATED APPLICATIONS

This application claims the benefit of U.S. Provisional Patent Application 63/317,674, filed Mar. 8, 2022, whose disclosure is incorporated herein by reference.

FIELD OF THE DISCLOSURE

The present disclosure relates generally to phacoemulsification systems, and particularly to detection and mitigation of vacuum surges in phacoemulsification systems.

BACKGROUND OF THE DISCLOSURE

A cataract is a clouding and hardening of the eye's natural lens, a structure which is positioned behind the cornea, iris and pupil. The lens is mostly made up of water and protein and as people age these proteins change and may begin to clump together obscuring portions of the lens. To correct this, a physician may recommend phacoemulsification cataract surgery. In the procedure, the surgeon makes a small incision in the sclera or cornea of the eye. Then a portion of the anterior surface of the lens capsule is removed to gain access to the cataract. The surgeon then uses a phacoemulsification probe, which has an ultrasonic handpiece with a needle. The tip of the needle vibrates at ultrasonic frequency to sculpt and emulsify the cataract while a pump aspirates particles and fluid from the eye through the tip. Aspirated fluids are replaced with irrigation of a balanced salt solution to maintain the anterior chamber of the eye. After removing the cataract with phacoemulsification, the softer outer lens cortex is removed with suction. An intraocular lens (IOL) is then introduced into the empty lens capsule restoring the patient's vision.

The present disclosure will be more fully understood from the following detailed description of the examples thereof, taken together with the drawings in which:

DETAILED DESCRIPTION OF EXAMPLES

Overview

Figure 1:
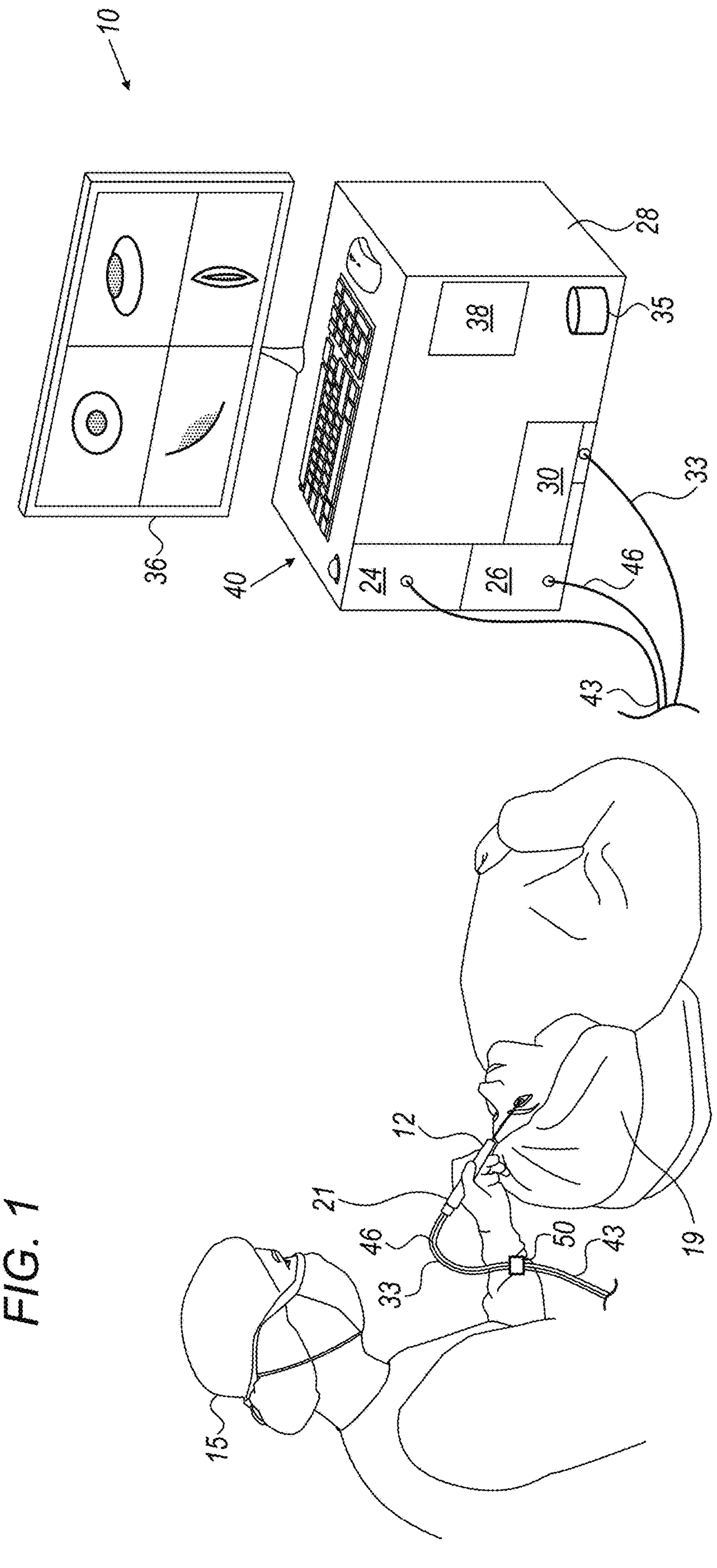
FIG. 1 is a schematic, pictorial view of a phacoemulsification system, in accordance with an example of the present disclosure.

During phacoemulsification of a cataracted lens of an eye, emulsified lens particles are aspirated via an aspiration line that runs through the phacoemulsification handpiece and further proximally to an aspiration pump. When a particle blocks the inlet of the aspiration line, the vacuum in the aspiration line increases. When the aspiration line later becomes unblocked (e.g., when the particle is subsequently sucked into the aspiration line), the high vacuum in the aspiration line resulting from the blockage may cause a vacuum surge with potentially traumatic consequences to the eye.

One possible way of avoiding the adverse effects of vacuum surges is to block the aspiration line upon detecting a vacuum surge. For example, an Anti-Vacuum Surge (AVS) module may be inserted in the aspiration and irrigation lines, or only in the aspiration line. The AVS module comprises a valve that is configured to cut-off the flow in the aspiration line. A processor, in the AVS module or in the phacoemulsification system console, may detect a vacuum surge, e.g., by reading a pressure or flow sensor coupled with the aspiration line, and close the valve. Techniques of this sort are described, for example, in U.S. patent application Ser. No. 17/130,409, filed Dec. 22, 2020, entitled "A module for Aspiration and Irrigation Control," which is hereby incorporated by reference.

Examples of the present disclosure provide improved methods and systems for operating AVS modules in phacoemulsification systems. In the present context, the term "AVS module" refers to any device that is inserted at least in the aspiration line for the purpose of detecting and mitigating vacuum surges.

In some examples, the phacoemulsification system comprises an optional extension tubing, which the physician may choose to insert between the phacoemulsification handpiece and the AVS module. In other words, the phacoemulsification system supports one configuration in which the AVS module is attached directly to the handpiece, and another configuration in which an extension tubing is inserted between the handpiece and the AVS module. A typical length of the extension tubing is in the range of twenty-three to twenty-eight centimeters, e.g., twenty-five centimeters. Some physicians may prefer to use the extension tubing, as it reduces the torque applied to the handpiece by the weight of the AVS module. Other physicians may prefer direct attachment of the AVS module to the handpiece.

The dual system configuration (with/without an extension tubing) is helpful for physicians, but on the other hand complicates the detection of vacuum surges. In practice, the extension tubing has a damping effect that modifies the characteristics of the vacuum surge as it is sensed at the AVS module. Typically, in the presence of an extension tubing, the vacuum surge will reach the AVS module with a smaller amplitude, longer duration and longer propagation delay, relative to a comparable vacuum surge in absence of an extension tubing. The differing characteristics make it difficult for the processor to detect vacuum surges reliably, e.g., to maximize the detection probability and minimize the probability of false detections.

In some examples, a processor of the phacoemulsification system overcomes the above-described challenge by automatically detecting whether an extension tubing is present. The processor then configures the system with a suitable parameter setting for detection of vacuum surges. The parameter setting may comprise, for example, one or more thresholds that are defined for the amplitude, slope and/or duration of the vacuum surge. By setting such thresholds depending on the detected system configuration (i.e., setting different thresholds depending on whether an extension tubing is present or not), vacuum surges can be detected and managed with high reliability.

In some examples, the processor detects the presence or absence of an extension tubing during a priming process applied by the physician to the handpiece. In a typical priming process, the tip of the handpiece is covered with a "priming chamber" or "test chamber"—a sealed cap that causes irrigation fluid to be fed-back into the aspiration line. In some examples, during the priming process, the processor applies a predefined irrigation-flow profile to the irrigation line. In one example the irrigation-flow profile is a "step function" profile. The processor then measures the aspiration-flow profile that occurs in the aspiration line, at the AVS module, in response to the predefined irrigation-flow profile.

Based on the characteristics of the aspiration-flow profile at the AVS module, the processor decides whether an extension tubing is present or absent. Typically, the processor checks whether the characteristics of the aspiration-flow profile are closer to those expected in a directly-attached AVS module or in an AVS module connected via an extension tubing. The processor may check, for example, amplitude of the aspiration-flow profile, a slope of the aspiration-flow profile, a duration of the aspiration-flow profile, and/or a delay of the aspiration-flow profile relative to the predefined irrigation-flow profile.

In summary, the disclosed techniques enable physicians to deploy an AVS module with or without an extension tubing, without compromising reliability in detection and management of vacuum surges.

System Description

FIG. 1 is a schematic, pictorial view of a phacoemulsification system 10 comprising a phacoemulsification probe ("handpiece") 12, in accordance with an example of the present disclosure.

Phacoemulsification probe 12 comprises a hollow needle, which is configured for insertion into a lens capsule of an eye of a patient 19 by a physician 15, for treating a cataract. During a phacoemulsification procedure, a pumping subsystem 24 in a console 28 pumps irrigation fluid from an irrigation reservoir (not shown), via an irrigation tubing line 43, to an irrigation sleeve coupled with and substantially surrounding the needle, for irrigating the eye. Eye fluid and waste matter (e.g., emulsified parts of the cataract) are aspirated via the hollow needle to a collection receptacle (not shown) by a pumping subsystem 26, also comprised in console 28, using an aspiration tubing line 46 running from probe 12 to console 28. In another example, pumping subsystem 24 may be coupled or replaced with a gravity-fed irrigation source such as a balanced salt solution bottle/bag.

In some examples, system 10 comprises an Anti-Vacuum Surge (AVS) module 50, coupled via suitable fluid connectors to the irrigation and aspiration lines. The AVS module is configured to control aspiration and irrigation flow rates, e.g., in order to reduce risks to the eye from irregular performance of aspiration and/or irrigation in probe 12, such as from vacuum surges caused by occlusion breaks at the tip of the needle. In the present example, the AVS module is coupled with the aspiration and irrigation lines externally to handpiece 12. The AVS module may be connected directly to a handle 21 of the handpiece, or via an extension tubing, as will be discussed below. Further aspects AVS modules are described in U.S. patent application Ser. No. 17/130,409, filed Dec. 22, 2020, entitled "A module for Aspiration and Irrigation Control," cited above.

In an example, the AVS module establishes variable fluid communication between aspiration line 46 and irrigation line 43, to control the flow of fluid between the two lines, so as to maintain pressures in the two lines within predefined limits. Moreover, the AVS module can discontinue aspiration, in order to provide a fast response (e.g., within several milliseconds) to a detected occlusion or vacuum surge. The AVS module may comprise its own processor and can be used with existing phacoemulsification systems as a disposable element to improve control over intraocular pressure (IOP) during the surgical cataract removal procedure. In some examples, a different type of AVS module can be used that is coupled only with the aspiration part of the system (i.e., without involving irrigation).

Phacoemulsification probe 12 includes other elements (not shown), such as a piezoelectric crystal coupled to a horn to drive vibration of the needle. The piezoelectric crystal may be configured to vibrate the needle in a resonant vibration mode. The vibration of the needle is used to break the cataract into small pieces during the phacoemulsification procedure. Console 28 comprises a piezoelectric drive module 30, coupled with the piezoelectric crystal, using electrical wiring running in a cable 33. Drive module 30 is controlled by a processor 38 and conveys processor-controlled driving signals via cable 33 to, for example, maintain the needle at maximal vibration amplitude. The drive module may be realized in hardware or software, for example, in a proportional-integral-derivative (PID) control architecture.

Processor 38 may receive user-based commands via a user interface 40, which may include setting a vibration mode, duty cycle, and/or frequency of the piezoelectric crystal, and setting or adjusting an irrigation and/or aspiration rate of the pumping subsystems 24/26. In an example, user interface 40 and display 36 may be combined as a single touch screen graphical user interface. In an example, the physician uses a foot pedal (not shown) as a means of control. Additionally or alternatively, processor 38 may receive the user commands from controls located in handle 21 of probe 12.

Some or all of the functions of processor 38 may be combined in a single physical component or, alternatively, implemented using multiple physical components. These physical components may comprise hard-wired or programmable devices, or a combination of the two. In some examples, at least some of the functions of processor 38 may be carried out by suitable software stored in a memory 35 (as shown in FIG. 1). This software may be downloaded to a device in electronic form, over a network, for example. Alternatively or additionally, the software may be stored in tangible, non-transitory computer-readable storage media, such as optical, magnetic, or electronic memory.

The system shown in FIG. 1 may include further elements which are omitted for clarity of presentation. For example, physician 15 typically performs the procedure using a stereomicroscope or magnifying glasses, neither of which are shown. Physician 15 may use other surgical tools in addition to probe 12, which are also not shown in order to maintain clarity and simplicity of presentation.

Figure 2:
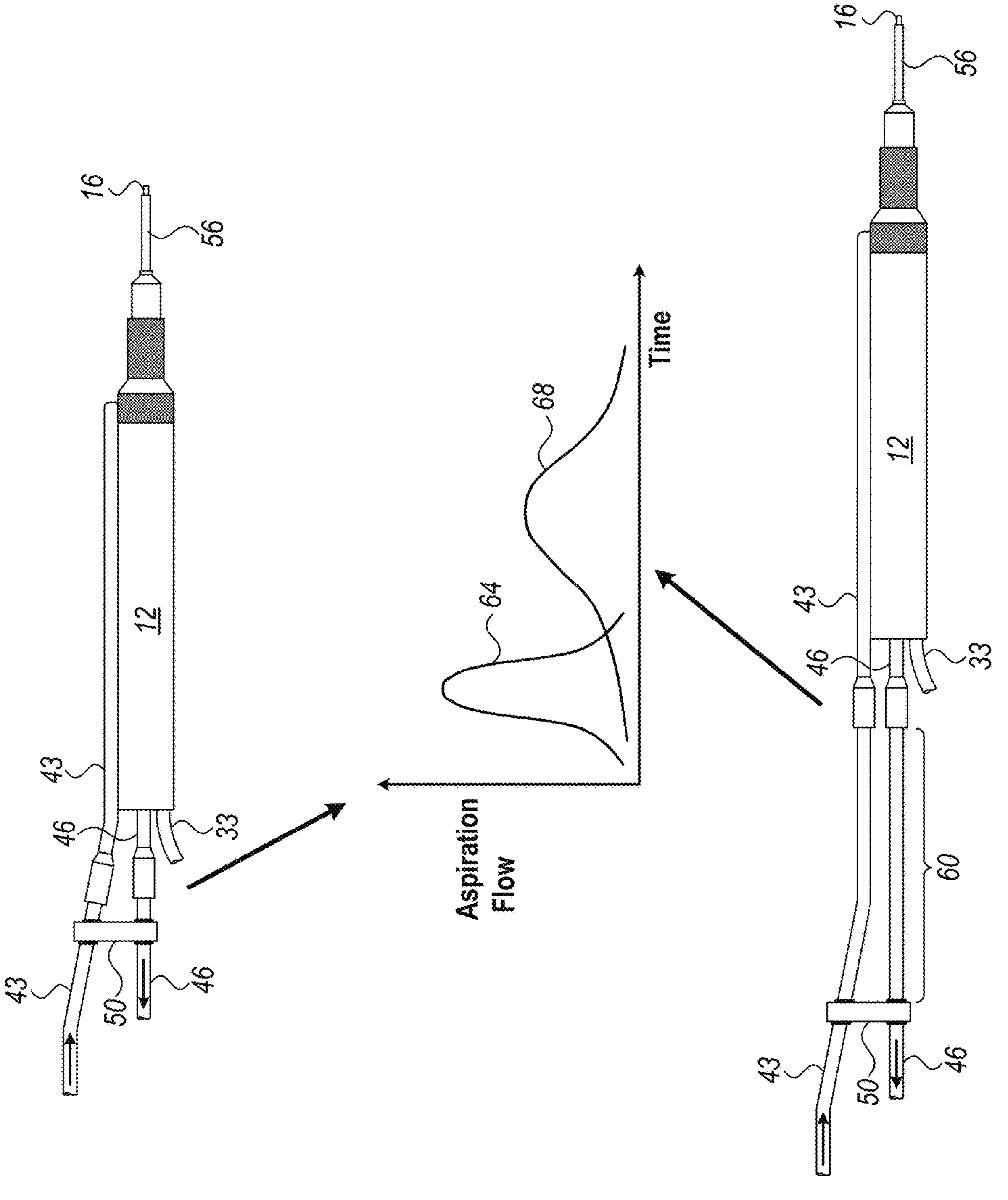
FIG. 2 schematically illustrates alternative configurations of a phacoemulsification system, with and without an extension tubing, and respective vacuum surge profiles, in accordance with an example of the present disclosure.

Configuration of Vacuum-Surge Detection Parameters Depending on Presence or Absence of Extension Tubing FIG. 2 schematically illustrates two alternative configurations of phacoemulsification system 10, in accordance with an example of the present disclosure. The figure also shows the structure of handpiece 12 in greater detail. In the present example, handpiece 12 comprises a coaxial irrigation sleeve 56 that at least partially surrounds needle 16 and creates a fluid pathway between the external wall of the needle and the internal wall of the irrigation sleeve. Needle 16 is hollow, so as to provide an aspiration pathway. The irrigation sleeve may have one or more side ports at or near its distal end, to allow irrigation fluid to flow toward the distal end of the handpiece through the fluid pathway and out of the port(s).

The top of FIG. 2 shows a system configuration in which AVS module 50 is attached directly or very close to handpiece 12. The bottom of FIG. 2 shows an alternative system configuration, in which an extension tubing 60 is inserted between AVS module 50 and handpiece 12. A typical length of the extension tubing is in the range of twenty-three to twenty-eight centimeters, e.g., twenty-five centimeters. This length range was found to strike a balance between ergonomic convenience to the physician and reliability in detecting and managing vacuum surges.

Typically, before starting the phacoemulsification procedure, physician 15 has the freedom to choose whether to use the top configuration (direct attachment without extension tubing) or the bottom configuration (with extension tubing).

The example depicted in the figure refers to an AVS module that is inserted both in irrigation line 43 and in aspiration line 46. As such, extension tubing 60 comprises an extension for the irrigation line and an extension for the aspiration line. In alternative examples, the AVS module and the extension tubing may be inserted only in aspiration line 46.

As noted above, AVS module 50 typically comprises a valve for cutting-off the flow in aspiration line 46. AVS module typically also comprises one or more flow, vacuum, or pressure sensors, for measuring the fluid pressure, vacuum, or flow in aspiration line 46 and/or in irrigation line 43. The terms "sensor", "flow sensor", "pressure sensor" and "vacuum sensor" are used interchangeably herein.

A graph in the middle of FIG. 2 illustrates profiles of vacuum surges that are typical of the two system configurations, as measured in aspiration line 46 at AVS module 50. The horizontal axis of the graph denotes time, and the vertical axis denotes pressure, vacuum or flow level in the aspiration line. A plot 64 illustrates a vacuum surge characteristic of the direct attachment configuration. A plot 68 illustrates a vacuum surge characteristic of the extension tubing configuration.

As seen, when AVS module 50 is attached directly to handpiece 12 (top configuration), the vacuum surge (plot 64) is typically strong in amplitude, has a steep slope and a short duration, and arrives at AVS module 50 after a small propagation delay. When AVS module 50 is connected to handpiece 12 via extension tubing 60 (bottom configuration), the vacuum surge (plot 68) is typically weaker in amplitude, has a more moderate slope, is longer in duration, and arrives at the AVS module after a longer propagation delay.

In some examples, processor 38 in console 28 detects such vacuum surges with high reliability, notwithstanding the differences in the surge characteristics between the two system configurations. Typically, processor 38 automatically detects the system configuration being used, i.e., detects whether extension tubing 60 is present between AVS module 50 and handpiece 12. Processor 38 then sets one or more parameters for vacuum-surge detection depending on the detected system configuration. In alternative examples, these tasks may be performed by a processor in AVS module 50, or jointly by processor 38 and a processor in the AVS module. For simplicity, the description that follows refers generally to "a processor" that carries out the disclosed technique.

Figure 3:
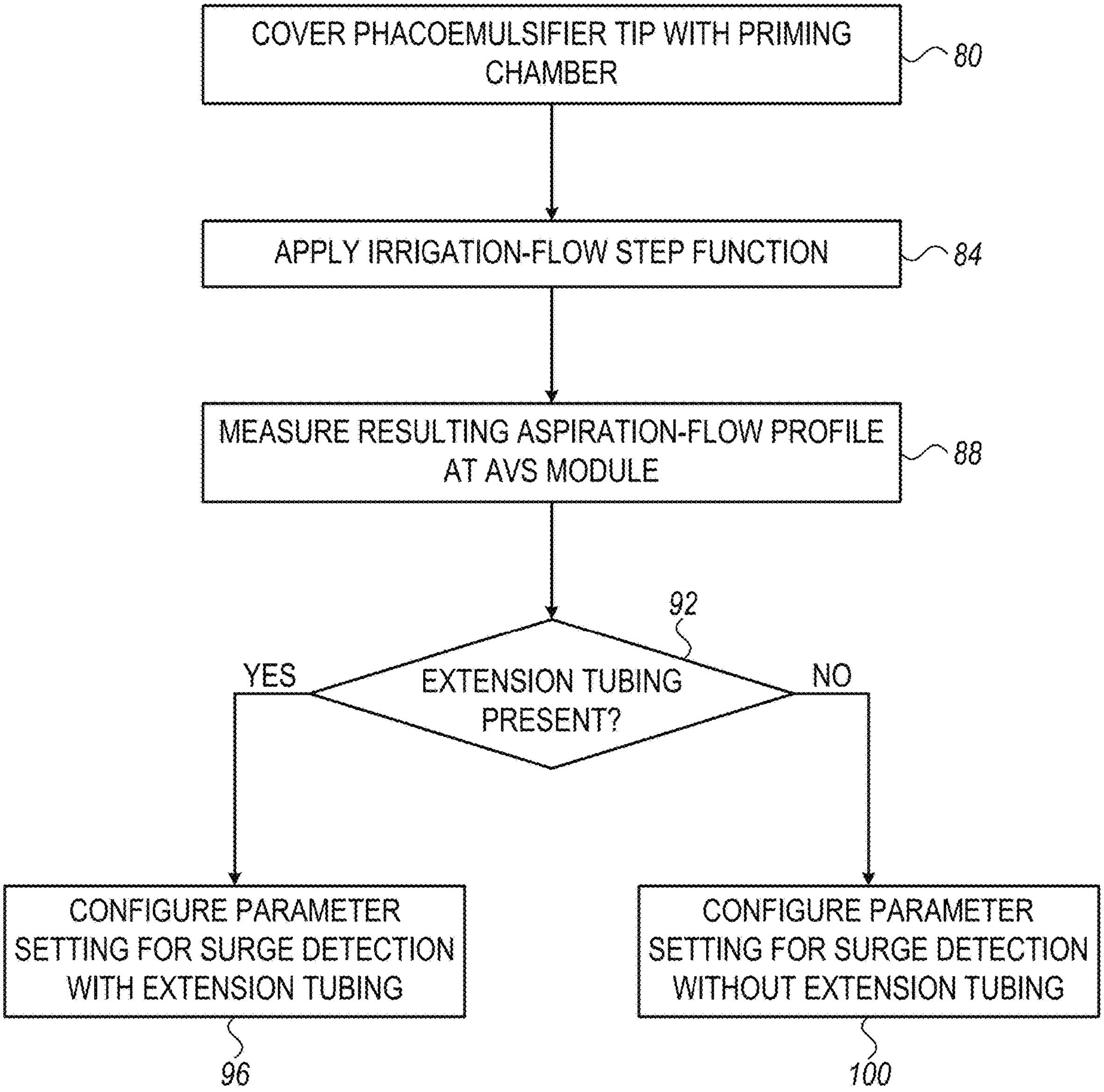
FIG. 3 is a flow chart that schematically illustrates a method for configuring vacuum-surge detection parameters, in accordance with an example of the present disclosure.

FIG. 3 is a flow chart that schematically illustrates a method for configuring vacuum-surge detection parameters in system 10, in accordance with an example of the present disclosure. In the present example, the method is carried out during a priming process that precedes the phacoemulsification procedure. The priming process aims to flush air from the system (e.g., from the irrigation and aspiration pumps, irrigation and aspiration lines, and needle 16). The priming process thus ensures that these system components are filled with fluid before the phacoemulsification procedure begins.

The method of FIG. 3 begins at a priming preparation stage 80. At this stage, physician 15 covers the tip of handpiece 12 with a "priming chamber" or "test chamber", which allows any irrigation fluid that flows out of the tip via the sleeve to flow back into aspiration line 46 via the needle.

At an irrigation stage 84, the processor instructs pumping subsystem 24 to pump a predefined irrigation-flow profile in irrigation line 43. The irrigation-flow profile typically comprises a "step function" profile, i.e., a substantially instantaneous transition from zero irrigation to a certain constant irrigation flow. Alternatively, however, any other suitable irrigation-flow profile can be used, e.g., an irrigation pulse having a predefined duration.

Since the tip of handpiece 12 is fitted with a priming chamber, the irrigation fluid pumped to the tip is reintroduced into aspiration line 46. At an aspiration measurement stage 88, the processor measures the aspiration-flow profile, at AVS module 50, resulting from the predefined irrigation-flow profile. The processor typically measures the aspiration-flow profile by reading a sensor that is coupled with aspiration line 46 at AVS module 50.

As explained above, if AVS module 50 is attached directly to handpiece 12, the measured aspiration-flow profile is expected to have a strong amplitude, a steep slope, a short duration, and to arrive at the AVS module with a small propagation delay relative to the irrigation-flow profile. When AVS module 50 is connected to handpiece 12 via extension tubing 60, the measured aspiration-flow profile is expected to be weaker in amplitude, to have a more moderate slope, to be longer in duration, and to arrives at the AVS module after a longer propagation delay relative to the irrigation-flow profile.

Note that the aspiration-flow profiles (with and without extension tubing 60) measured during priming may differ from the aspiration-flow profiles (with and without extension tubing 60) observed following occlusion break during an actual procedure. One reason for the difference is that the irrigation step-function profile (applied during priming) may differ from the profile of an occlusion break (experienced during a real-life procedure). Notwithstanding such differences, the aspiration-flow profiles measured during priming enable the processor to decide whether extension tubing 60 is present or absent.

In a typical example, the step-function response of aspiration line 46 has a propagation delay of approximately 40 ms for every 1.5 m length of tubing. The step-function response is typically dispersive, i.e., low-frequency pressure waves move faster than high-frequency pressure waves along the aspiration line. Thus, for a 25 cm extension tubing, the peak of the step-function response will be delayed by approximately 25*40/150 ms=~6.67 ms. This would be the expected time difference between the peaks of the aspiration-flow profiles measured with and without extension tubing 60.

At a configuration detection stage 92, the processor uses any or all of the above characteristics to identify whether or not extension tubing 60 is present between AVS module 50 and handpiece 12.

If an extension tubing is found to be present, the processor configures a parameter setting that is suitable for detecting vacuum surges in the presence of an extension tubing, at an extension configuration stage 96. If an extension tubing is found to be absent, the processor configures a (different) parameter setting that is suitable for detecting vacuum surges in absence of an extension tubing, at a direct-attachment configuration stage 100.

The parameter settings may differ from one another in various parameters. For example, the processor may declare a vacuum surge if the amplitude of the surge exceeds a threshold. In this example the processor may set the threshold to a certain value for the direct-attachment configuration, and to a different value (e.g., lower) for the extension-tubing configuration. As another example, the processor may declare a vacuum surge if the slope of the surge exceeds a threshold. In this example the processor may set the threshold to a certain value for the direct-attachment configuration, and to a different (e.g., lower) value for the extension-tubing configuration.

As yet another example, the processor may declare a vacuum surge if the duration of the surge is below a threshold. As noted above, the response of the aspiration line is dispersive. therefore, a surge will typically have a longer duration when extension tubing 60 is present, and a shorter duration in a direct-attachment configuration. In this example the processor may set the threshold to a certain value for the direct-attachment configuration, and to a larger value for the extension-tubing configuration. In some examples, the processor may use a combination of multiple such thresholds, or any other suitable threshold or other mechanism.

EXAMPLES

Example 1: A phacoemulsification system includes a phacoemulsification handpiece, an irrigation line and an aspiration line connected to the phacoemulsification handpiece, an Anti-Vacuum Surge (AVS) module inserted at least in the aspiration line, and a processor. The processor is configured to automatically detect whether an extension tubing is present in the aspiration line between the phacoemulsification handpiece and the AVS module, to set a first parameter setting, for detecting vacuum surges in the aspiration line, in response to detecting that the extension tubing is present, and, in response to detecting that the extension tubing is not present, to set a second parameter setting, different from the first parameter setting, for detecting the vacuum surges in the aspiration line.

Example 2: The phacoemulsification system according to example 1, wherein the processor is configured to detect whether the extension tubing is present by reading at least one sensor in the AVS module.

Example 3: The phacoemulsification system according to example 1, wherein the processor is configured to detect whether the extension tubing is present by applying a predefined irrigation-flow profile to the irrigation line, and measuring an aspiration-flow profile occurring in the aspiration line, at the AVS module, in response to the predefined irrigation-flow profile.

Example 4: The phacoemulsification system according to example 3, wherein the predefined irrigation-flow profile includes a step function.

Example 5: The phacoemulsification system according to example 3, wherein the processor is configured to measure the aspiration-flow profile during a priming process applied to the phacoemulsification handpiece.

Example 6: The phacoemulsification system according to example 3, wherein the processor is configured to detect whether the extension tubing is present by measuring one or more of: an amplitude of the aspiration-flow profile; a slope of the aspiration-flow profile; a duration of the aspiration-flow profile; and a delay of the aspiration-flow profile relative to the predefined irrigation-flow profile.

Example 7: The phacoemulsification system according to example 1, wherein the first and second parameter settings differ from one another in one or more thresholds defined for one or more characteristics of a pressure profile measured in the aspiration line.

Example 8: The phacoemulsification system according to example 7, wherein the one or more characteristics include at least one of an amplitude, a slope and a duration of the pressure profile in the aspiration line.

Example 9: A phacoemulsification system includes a phacoemulsification handpiece, an irrigation line and an aspiration line connected to the phacoemulsification handpiece, an Anti-Vacuum Surge (AVS) module inserted at least in the aspiration line, and an extension tubing, which is inserted at least in the aspiration line between the phacoemulsification handpiece and the AVS module.

Example 10: The phacoemulsification system according to example 9, wherein a length of the extension tubing is between twenty-three and twenty-eight centimeters.

Example 11: A method in a phacoemulsification system that includes a phacoemulsification handpiece, an irrigation line and an aspiration line connected to the phacoemulsification handpiece, and an Anti-Vacuum Surge (AVS) module inserted at least in the aspiration line. The method includes automatically detecting whether an extension tubing is present in the aspiration line between the phacoemulsification handpiece and the AVS module. In response to detecting that the extension tubing is present, a first parameter setting is set for detecting vacuum surges in the aspiration line. In response to detecting that the extension tubing is not present, a second parameter setting, different from the first parameter setting, is set for detecting the vacuum surges in the aspiration line. A vacuum surge in the aspiration line is detected in accordance with the set first or second parameter setting.

It will thus be appreciated that the examples described above are cited by way of example, and that the present disclosure is not limited to what has been particularly shown and described hereinabove. Rather, the scope of the present disclosure includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A phacoemulsification system, comprising:
- a phacoemulsification handpiece;
- an irrigation line and an aspiration line connected to the phacoemulsification handpiece;
- an Anti-Vacuum Surge (AVS) module inserted at least in the aspiration line; and
- a processor, configured to:
  - automatically detect whether an extension tubing is present in the aspiration line between the phacoemulsification handpiece and the AVS module;

in response to detecting that the extension tubing is present, set a first parameter setting for detecting vacuum surges in the aspiration line; and in response to detecting that the extension tubing is not present, set a second parameter setting, different from the first parameter setting, for detecting the vacuum surges in the aspiration line.

2. The phacoemulsification system according to claim 1, wherein the processor is configured to detect whether the extension tubing is present by reading at least one sensor in the AVS module.

3. The phacoemulsification system according to claim 1, wherein the processor is configured to detect whether the extension tubing is present by applying a predefined irrigation-flow profile to the irrigation line, and measuring an aspiration-flow profile occurring in the aspiration line, at the AVS module, in response to the predefined irrigation-flow profile.

4. The phacoemulsification system according to claim 3, wherein the predefined irrigation-flow profile comprises a step function.

5. The phacoemulsification system according to claim 3, wherein the processor is configured to measure the aspiration-flow profile during a priming process applied to the phacoemulsification handpiece.

6. The phacoemulsification system according to claim 3, wherein the processor is configured to detect whether the extension tubing is present by measuring one or more of:

an amplitude of the aspiration-flow profile;

a slope of the aspiration-flow profile;

a duration of the aspiration-flow profile; and a delay of the aspiration-flow profile relative to the predefined irrigation-flow profile.

7. The phacoemulsification system according to claim 1, wherein the first and second parameter settings differ from one another in one or more thresholds defined for one or more characteristics of a pressure profile measured in the aspiration line.

8. The phacoemulsification system according to claim 7, wherein the one or more characteristics comprise at least one of an amplitude, a slope and a duration of the pressure profile in the aspiration line.

9. A method performed by a processor in a phacoemulsification system that includes a phacoemulsification handpiece, an irrigation line and an aspiration line connected to the phacoemulsification handpiece, and an Anti-Vacuum Surge (AVS) module inserted at least in the aspiration line, the method comprising:

automatically detecting whether an extension tubing is present in the aspiration line between the phacoemulsification handpiece and the AVS module;

in response to detecting that the extension tubing is present, setting a first parameter setting for detecting vacuum surges in the aspiration line;

in response to detecting that the extension tubing is not present, setting a second parameter setting, different from the first parameter setting, for detecting the vacuum surges in the aspiration line; and detecting a vacuum surge in the aspiration line in accordance with the set first or second parameter setting.

10. The method according to claim 9, wherein automatically detecting whether the extension tubing is present comprises reading at least one sensor in the AVS module.

11. The method according to claim 9, wherein automatically detecting whether the extension tubing is present comprises applying a predefined irrigation-flow profile to the irrigation line, and measuring an aspiration-flow profile occurring in the aspiration line, at the AVS module, in response to the predefined irrigation-flow profile.

12. The method according to claim 11, wherein applying the predefined irrigation-flow profile comprises applying a step function.

13. The method according to claim 11, wherein measuring the aspiration-flow profile is performed during a priming process applied to the phacoemulsification handpiece.

14. The method according to claim 11, wherein automatically detecting whether the extension tubing is present comprises measuring one or more of:

an amplitude of the aspiration-flow profile;

a slope of the aspiration-flow profile;

a duration of the aspiration-flow profile; and a delay of the aspiration-flow profile relative to the predefined irrigation-flow profile.

15. The method according to claim 9, wherein the first and second parameter settings differ from one another in one or more thresholds defined for one or more characteristics of a pressure profile measured in the aspiration line.

16. The method according to claim 15, wherein the one or more characteristics comprise at least one of an amplitude, a slope and a duration of the pressure profile in the aspiration line.

* * * * *